US009700620B2

(12) United States Patent
Almutairi et al.

(10) Patent No.: US 9,700,620 B2
(45) Date of Patent: Jul. 11, 2017

(54) POLYMERIC NANOCARRIERS WITH LIGHT-TRIGGERED RELEASE MECHANISM

(71) Applicant: THE REGENTS OF THE UNIVERSITY OF CALIFORNIA, Oakland, CA (US)

(72) Inventors: Adah Almutairi, La Jolla, CA (US); Mathieu Lessard-Viger, San Diego, CA (US); Wangzhong Sheng, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/213,310

(22) Filed: Jul. 18, 2016

(65) Prior Publication Data
US 2016/0324966 A1 Nov. 10, 2016

Related U.S. Application Data

(62) Division of application No. 14/424,963, filed as application No. PCT/US2013/057169 on Aug. 28, 2013, now abandoned.
(Continued)

(51) Int. Cl.
G06F 19/18 (2011.01)
G06F 19/20 (2011.01)
(Continued)

(52) U.S. Cl.
CPC ........ A61K 41/0028 (2013.01); A61K 9/0004 (2013.01); A61K 9/5031 (2013.01);
(Continued)

(58) Field of Classification Search
CPC .............. A61K 41/0028; A61K 9/0004; A61K 9/5031; A61K 9/5153; A61N 2005/0658;
(Continued)

(56) References Cited

U.S. PATENT DOCUMENTS 6,471,968 B1 10/2002 Baker, Jr. et al.
7,018,624 B2 3/2006 Harris
(Continued)

FOREIGN PATENT DOCUMENTS

WO 2004019993 A1 3/2004
WO 2007146426 A2 12/2007
WO 2010104819 A2 9/2010

OTHER PUBLICATIONS

Fomina et al. (Photochemical mechanisms of light-triggered release from nanocarriers, Adv Drug Deliv Rev. 2012;64(11):1005-1020).*
(Continued)

Primary Examiner — Ernst V Arnold
(74) Attorney, Agent, or Firm — Eleanor Musick; Musick Davison LLP

(57) ABSTRACT

Near infrared radiation at a wavelength that induces resonance in water is used to remotely activate thermal plasticization of polymeric particles to trigger the release of encapsulated molecules from the particles. Nanocarriers formed from biocompatible hydrophilic polymers may be used to deliver encapsulated molecules to tissue with a reversible transition that allows repeated activations for extended release of the payload.

9 Claims, 11 Drawing Sheets

Related U.S. Application Data

(60) Provisional application No. 61/694,179, filed on Aug. 28, 2012.

(51) Int. Cl.

| | | |
|---|---|---|
| *A61K 41/00* | (2006.01) | |
| *A61K 9/00* | (2006.01) | |
| *A61K 9/51* | (2006.01) | |
| *A61N 5/06* | (2006.01) | |
| *A61K 9/50* | (2006.01) | |

(52) U.S. Cl.
CPC ............ *A61K 9/5153* (2013.01); *A61N 5/062* (2013.01); *A61N 2005/0658* (2013.01)

(58) Field of Classification Search
CPC ......... A61N 5/062; G06F 19/18; G06F 19/20; G06F 19/326; G06F 19/3456
See application file for complete search history.

(56) References Cited

U.S. PATENT DOCUMENTS

| | | |
|---|---|---|
| 8,758,778 B2 | 6/2014 | Almutairi et al. |
| 8,828,383 B2 | 9/2014 | Almutairi et al. |
| 2005/0271615 A1 | 12/2005 | Shabat et al. |
| 2006/0069230 A1 | 3/2006 | Papisov |
| 2006/0269480 A1 | 11/2006 | Amir et al. |
| 2007/0009980 A1 | 1/2007 | Graham et al. |
| 2007/0148074 A1 | 6/2007 | Sadoqi et al. |
| 2009/0169628 A1 | 7/2009 | Gabriele et al. |
| 2009/0233359 A1 | 9/2009 | Kwon |

OTHER PUBLICATIONS

Wilson, D.S. et al., "Orally delivered thioketal nanoparticles loaded with TNF-α-siRNA target inflammation and inhibit gene expression in the intestines", 2009, Nature Materials, pp. 923-928.
Alexis, F., et al., "HER-2-Targeted Nanoparticle-Athbody Bioconjugates for Cancer Therapy", 2008, Cem MedChem, pp. 1839-1843.
Xu, L., et al, "Effects of Temperature and pH on the Degradation of Poly(lactic acid) Brushes", 2011, Macromolecules, pp. 4777-4782.
Andersson, L., et al., "Poly(ethylene glycol)-Poly(ester-carbonate) Block Copolymers Carrying PEG-Peptidyl-Doxorubicin Pendant Side Chains: Synthesis and Evaluation as Anticancer Conjugates", 2005, Biomacromolecules, pp. 914-926.
Sankaranarayanan, J., et al., "Multiresponse Strategies to Modulate Burst Degradation and Release from Nanoparticles", 90/90/2010, ACS Nano, pp. 5930-5936.
Mahmoud, E.A., et al., "Inflammation Responsive Logic Gate Nanoparticles for the Delivery of Proteins", 2011, Bioconjugate Chem., 22, pp. 1416-1421.
Fomina, N., et al., "UV and Near-IR triggered release from polymeric nanoparticles", Jul. 21, 2010, J Am Chem Soc., 132(28): 9540-9542.
Huotari, J., et al., "Endosome Maturation", 2011, The EMBO Journal, (30) 3481-3500.
Sagi, A., et al., "Self-Immolative Polymers", 2008, J. Am Chem Soc., 130(16): 5434-5435.
Kneipp, J., et al., "Two-photon vibrational spectroscopy for biosciences based on surface-enhanced hyper-Raman scattering", 2006, PNAS, (103(46): 17149-17153.
Furuta, T., et al., "Brominated 7-hydroxycoumarin-4-ymethyls: Photolabile protecting groups with biologically useful cross-sections for two photon photolysis", 1999, PNAS vol. 96, pp. 1193-1200.
Gil, P.R., et al., "Composite Nanoparticles Take Aim at Cancer", 2008, ACS Nano, 2(11):2200-2205.
Amir, R.J., et al., "Prodrug Activation Gated by a Molecular "OR" Logic Trigger", 2005, Angew. Chem. Int. Ed., vol. 44, pp. 2-4.
Flomenbom, O., et al., "Some new aspects of dendrimer applications", 2005, J. Luminescence, vol. 111, pp. 315-325.
Bedard, M. F., et al., "Polymeric microcapsules with light responsive properties of encapsulation and release", 2010, Advances in Colloid and Interface Science, vol. 158, pp. 2-14.
Bedard, M.F., et al., "Toward Self-Assembly of Nanoparticles on Polymeric Microshells: Near-IR Release and Permeability", 2008, ACS Nano; 2(9): 1807-1816.
Medina, S.H., et al., "Dendrimers as Carriers for Delivery of Chemotherapeutic Agents", 2009, Chem. Rev., 109, pp. 3141-3157.
Singh, S.K., et al., "Dendrimer a versatile polymer in drug discovery", 2009, Asian J Pharm., 3:178-187.
Sopczynski, B.P., "A New Anti-Tumor Drug Delivery System: Dendrimers", 2008, MMG 445 Basic Biotechnology eJournal, 2:87-92.
Weinstain, R., et al., "Self-Immolative Comb-Polymers: Multiple-Release of Side-Reporters by a Single Stimulus Event", 2008, Chem. Eur. J., 14:6857-6861.
Crampton, H.L., et al., "Dendrimers as drug delivery vehicles: non-covalent interactions of bioactive compounds with dendrimers", Mar. 2, 2007, Polym. Int., 56(4): 489-496.
Wu, G. et al., "Remotely triggered liposomal release by near-infrared absorption via hollow gold nanoshells", J. Am Chem Soc. Jul. 2, 2008, 130(26): 8175-8177.
Almeria, B., et al., "Controlling the morphology of electrospray-generated PLGA microparticles for drug delivery", J. Colloid and Interface Science, 2010, 343: 125-133.
Hribar, K.C., "Enhanced Release of Small Molecules from Near-Infrared Light Responsive Polymer-Nanorod Composites", ACS Nano, 2011, 5(4):2948-2956.
International Preliminary Report on Patentability for PCT/US2013/057169, mailed Mar. 3, 2015, 3 pages.
Written Opinion for PCT/US2013/057169, mailed Nov. 28, 2013, 3 pages.
Chu, C., et al., "Surface deformation of gold nanorod-loaded poly(DL-lactide-co-glycolide) nanoparticles after ear infrared irradiation: an active and controllable drug release system", J. Mater. Chem., 2010, 20 : 3260-3264.
Makadia, H.K., et al., "Poly Lactic-co-Glycolic Acid (PLGA) as Biodegradable Controlled Drug Delivery Carrier," Polymers 2011, 3 : 1377-1379.
Extended European Search Report for EP 13832829.9 issued Jan. 8, 2016, 6 pages.

\* cited by examiner

POLYMERIC NANOCARRIERS WITH LIGHT-TRIGGERED RELEASE MECHANISM

RELATED APPLICATIONS

The present application is a divisional of U.S. application Ser. No. 14/424,963, filed Feb. 27, 2015, which is a 371 national stage filing of International Application No. PCT/US2013/057169, filed Aug. 28, 2013, which claims the benefit of the priority of U.S. Provisional Application No. 61/694,179, filed Aug. 28, 2012. The disclosure of the listed applications are incorporated herein by reference in their entirety.

GOVERNMENT RIGHTS

This invention was made with government support under Grant No. OD006499 awarded by the National Institutes of Health. The government has certain rights in the invention.

FIELD OF THE INVENTION

The present invention relates to polymeric nanocarriers for biomedical applications and a method for light-triggered release from such nanocarriers.

BACKGROUND OF THE INVENTION

Light-triggered release from polymeric capsules is a key tool for delivering encapsulated molecules to targeted tissues with spatial and temporal control. Systems that respond to near-infrared (NIR) wavelengths (650-1300 nm) are particularly attractive due to the deep penetration depth with low attenuation, which allow low NIR irradiation to penetrate through several centimeters of tissue with minimal cytotoxicity. Use of NIR as a trigger for release of drugs from polymer nanocarriers is an active area of research, however, the approaches reported thus far experience significant drawbacks that limit their biomedical relevance.

In one common approach, gold or other metal nanostructures are incorporated into polymer capsules to generate heat upon absorption of NIR light, loosening the surrounding polymer matrix to release therapeutics. This approach is limited by the controversial biocompatibility of metal nanostructures as well as the considerable heat they generate upon NIR absorption, which may be detrimental to tissue. For example, temperature changes as high as ~40° C. following 30 minutes of irradiation at 1.1 W, and from room temperature to boiling of aqueous solution in 5 min at 1.5 W have been reported. This excessive heating of the surroundings could potentially damage cells. This gold-assisted thermal plasticization concept is also known to be limited to heat-stable cargo, as the temperature rise around the metal particle has been shown to be well above 250° C. Over time, extensive irradiation of gold nanostructures with high power NIR light can also cause irreversible damage to the metal nanoparticles through melting, diminishing their photothermal responsiveness over time.

Alternatively, nanocarriers can also be formulated from polymers containing photo-responsive modalities that respond through chemical changes such as isomerization, oxidation, dimerization, and bond cleavage. In order to make use of the inherently low energy of NIR light, these mechanisms all require simultaneous two-photon absorption, necessitating the use of high powered and focused pulsed NIR lasers, with energies that may exceed the damage threshold of biological tissue. Recently, the limitations of two-photon photochemistry have been overcome by coupling the photosensitive polymer nanocarriers to lanthanide-doped up-converting nanoparticles (UCNPs) that sequentially absorb multiple NIR photons and convert them into higher-energy photons in the UV region. Because simultaneous absorption of excitation photons is not required, UCNPs provide for triggered release in response to biologically benign excitation power densities. However, UCNPs contain rare-earth heavy elements that may prove to be toxic in vitro and in vivo.

Although of great interest for some application, these strategies all have significant barriers to widespread application, especially for biomedical uses. Accordingly, there is a need for more biologically benign strategies to obtain remote-controlled photo-release using NIR light that would overcome these limitations.

BRIEF SUMMARY

According to the present invention, confined water within biodegradable polymer particles is selectively heated using NIR light to induce release of a payload contained within the particles. The polymer particles, which are formed from materials lacking inherent light sensitivity, undergo thermal plasticization when exposed to low power NIR light, inducing a phase change that allows the encapsulated payload to diffuse out of the particle. Using this approach, instantaneous and controlled release of a payload can be achieved using a continuous-wave NIR laser at powers as low as 170 mW without significant heating of the surrounding aqueous solution.

In one embodiment, continuous wave NIR laser light may be used to selectively heat trace amounts of water that is present in most polymer particles, causing thermal plasticization of the polymer particles, increasing their diffusivity enough to release encapsulated compounds without polymer degradation. The wavelength of the NIR light is selected to produce resonance in the water, within a range of about 980 nm to 1200 nm. In an exemplary embodiment, the particles may be formed from poly(lactic-co-glycolic acid) (PLGA), however, other polymer matrices may be used. Multiple consecutive NIR exposures can be used to release multiple payload doses without causing irreversible rupture of the carriers. The on-demand rate of release is dependent on the average NIR photon energy administered to the system and inversely proportional to the size of the particles, both of which can be used to control the amount of released material.

This NIR-induced thermal plasticization-based release mechanism provides additional benefits over existing technologies including wavelength sensitivity, low light intensity requirements and broad applicability to a wide variety of encapsulated compounds.

Upon heating of the micro-particles suspended in solution, the polymer loses its particle morphology and clumping occurs. At low temperatures, the clumping is reversible via sonication whereas heating to temperatures greater than ~60° C. for greater than ~5 minutes results in irreversible clumping of the polymer. In general, when a payload is encapsulated, heating to temperatures greater than the glass transition temperature of the polymer results in release of the payload, and heating to temperatures greater than ~60° C. results in maximum release of payload. The application of 980 nm NIR radiation at 500 mW for 15 min on suspended micro-particles at 37° C. results in substantial, but reversible aggregation of the polymer.

There are many useful applications for the present invention, which provides on-demand delivery of small molecules to cells or within living organisms (up to a few centimeters deep). Given the enormous impact that NIR uncaging of neurotransmitters has had on neuroscience, use of the inventive particles to deliver virtually any small molecule could provide answers to questions concerning normal and pathological development. The inventive delivery method could be commercialized by mass production of PLGA (or other widely available polymer) particles encapsulating pharmacological agents commonly used in cell biology, or as a new application of existing polymers, as polymer producing companies could provide formulation protocols. For example, well dispersed PLGA micro-particles encapsulating a therapeutic payload could be readily injected into the eye using a micro-needle. Typically, PLGA has a short retention time (2-3 months) inside the body due to degradation via breakage of ester bonds in the polymer backbone. However, if a laser were to be used to induce aggregation and/or clumping of the particles into a large drug reservoir, the retention time of the drug could be increased for longer-term release. In one aspect of the invention, a nanocarrier for delivering a payload comprises a polymer particle adapted for encapsulating molecules, wherein the polymer comprises nanodomains of water and undergoes a phase change upon irradiation with NIR light that allows at least a portion of the encapsulated molecules to diffuse out of the particle. The phase change is preferably reversible and the polymer may have no inherent light sensitivity. The NIR light has a wavelength of 980 nm. The polymer may be poly(lactic-co-glycolic acid) (PLGA) with a lactide:glycolide ratio selected according to a desired release rate or desired particle size. The encapsulated molecules may be a therapeutic compound or a dye. An aggregation of nanocarriers may be used for delivery of the payload over an extended period of time.

In another aspect of the invention, a particle for delivering a payload to targeted tissue comprises a hydrophilic polymer having a payload encapsulated therein, where the polymer undergoes a photothermal transition when irradiated with NIR light whereby at least a portion of the payload diffuses out of the particle. The NIR light preferably has a wavelength of 980 nm and the photothermal transition is reversible. The polymer may be poly(lactic-co-glycolic acid) (PLGA) with a lactide:glycolide ratio selected according to a desired release rate or a desired particle size. The encapsulated payload may be a therapeutic compound or a dye. An aggregation of particles may be used for delivery of the payload over an extended period of time.

In another aspect of the invention, a method for delivering a payload comprises encapsulating the payload in a nanocarrier comprising a hydrophilic polymer having no inherent light sensitivity; hydrating the polymer to form nanodomains of water; and exposing the nanocarrier to light having a wavelength adapted to induce resonant photon interactions with the water to locally heat the polymer to induce a phase change in the polymer whereby the payload diffuses out of the nanocarrier. The light is preferably NIR light having a wavelength of 980 nm. The polymer may be poly(lactic-co-glycolic acid) (PLGA) with a lactide:glycolide ratio selected according to a desired release rate or desired particle size. The payload may be a therapeutic compound or a dye. An aggregation of nanocarriers may be formed for delivery of the payload over an extended period of time.

BRIEF DESCRIPTION OF THE DRAWINGS

FIG. 1A shows the dry nanostructure, FIG. 1B shows the particle after hydration to form isolated nanodomains of water in the nanostructure; FIG. 1C shows the heating of water in the nanostructure with NIR light, and FIG. 1D shows release of encapsulated molecules following photothermal heating of water droplets inside the particles.

DETAILED DESCRIPTION

Figure 1A:
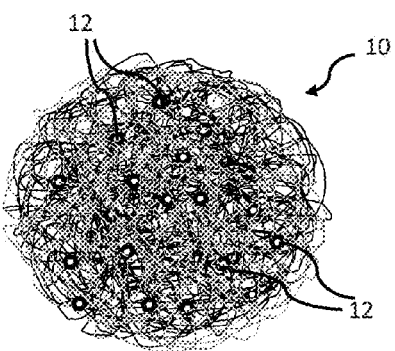
FIGS. 1A-1D are a schematic representation of NIR-induced release through thermal plasticization, where
Figure 1B:
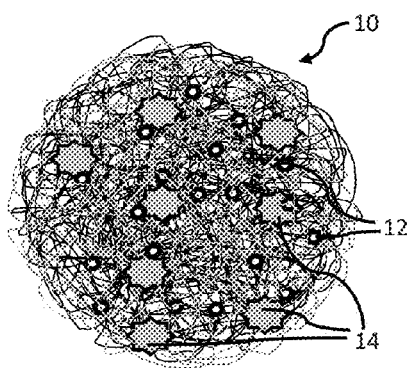
Figure 1C:
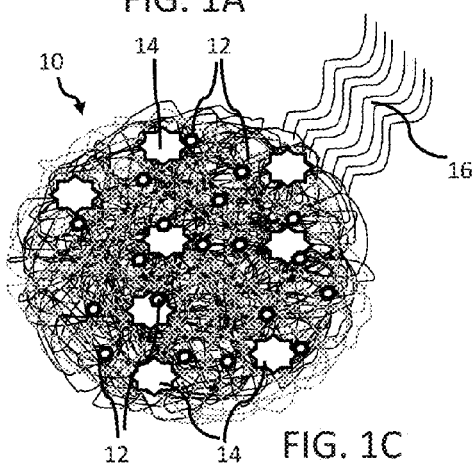
Figure 1D:
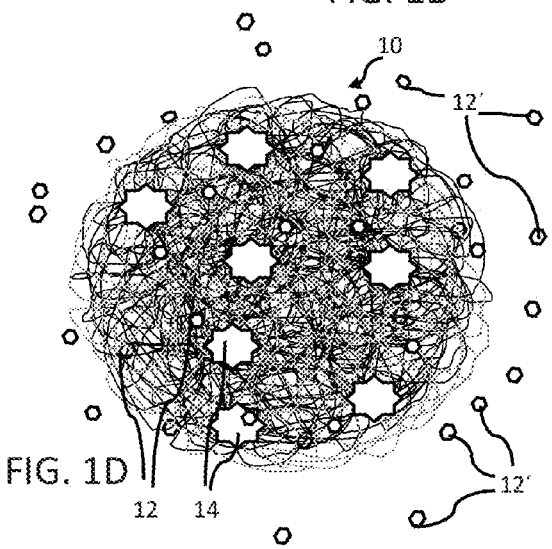
Figure 2:
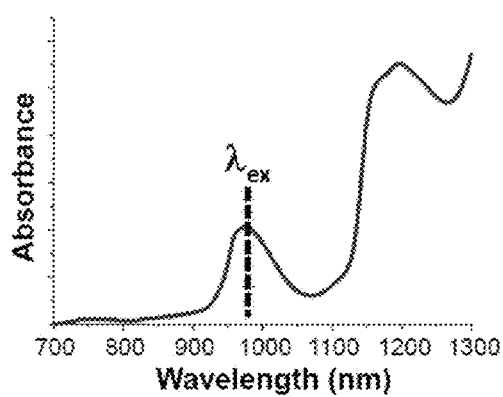
FIG. 2 is a plot of the absorption spectrum of water in the NIR region.
Figure 3:
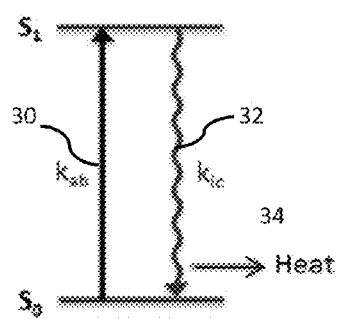
FIG. 3 schematically illustrates the transformation of absorbed photonic energy into heat through internal conversion.

According to the present invention, NIR radiation is used to achieve controlled release of an encapsulated payload from inherently non-light-sensitive polymer microparticles by exploiting the unusual behavior of water confined within the particle microstructure. FIGS. 1A-1D provide a schematic representation of NIR-induced release through thermal plasticization. FIG. 1A shows a dry particle 10 with encapsulated payload 12. The particles are hydrated by dispersion in water. The uptake of water in the polymer matrix forms isolated nanodomains of water 14 in the nanostructure, as shown in FIG. 1B. In FIG. 1C, irradiation with NIR light 16 at the appropriate wavelength produces photothermal heating of the confined water droplets 14 inside the polymer particles 10. FIG. 2 is a plot of the absorption spectrum of water in the NIR region, showing peak absorption at 980 nm. The conductive heat transfer to the polymer matrix causes the polymer to become rubbery, allowing the payload to diffuse out of the particles. FIG. 3 is a schematic representation showing how the water molecules, initially at state $S_0$, are excited to state Si via photon absorption ($k_{ab}$) 30 and the excitation energy ($k_{ic}$) 32 is converted into heat 34. FIG. 1D shows the release of encapsulated molecules (released payload 12') following photothermal heating of the particles 10. Controlled heating and selection of particle parameters may provide for the partial release of payload molecules in response to a single irradiation event, leaving some of the payload 12 within the particle 10 for later release using NIR light.

In the exemplary embodiment, poly(lactic-co-glycolic acid) (PLGA) was selected as the polymer matrix because it is FDA-approved, widely used for a variety of biomaterials applications, and extensively studied as a drug carrier. In an aqueous environment, biodegradable polymers such as PLGA swell and take up water, forming isolated nanodomains within the amorphous regions of the polymer microstructure (see FIG. 1B). Interestingly, confinement of nano-sized droplets of water within the micro-scale geometries of polymer particles has an effect on the glass transition temperature (Tg) of the polymer. Nano-sized droplets of water behave as plasticizers within the polymer matrix by increasing the free volume of the polymer chains and consequently depressing the Tg of the polymer. In addition, confined water inside polymeric matrices behaves differently from bulk water in terms of its response to resonant laser irradiation. Upon exposure to resonant wavelengths of NIR light, water molecules are excited via photon absorption and the excitation energy is converted into heat.

The NIR wavelength was selected to allow effective photon-to-thermal energy conversion and biologically relevant penetration depth, limiting the range to wavelengths shorter than 1300 nm. Below this limit, water absorbs wavelengths around 1200 and 980 nm. Because 1200 nm lasers are not readily available, 980 nm light was selected for this study. When irradiated with 980 nm NIR light, in the case of bulk water, the energy is rapidly dissipated via diffusive heat transfer. However, due to shielding from the external bulk water by the polymer, submicron water droplets trapped inside polymer microstructures dissipate energy via conductive heat transfer to the constituting polymer matrix. Consequently, exposure to resonant NIR laser radiation can be used to increase internal droplet temperature without significant heating of the bulk solution. This localized heating of the polymer matrix appears to induce a thermal phase change through the $T_g$, causing the amorphous regions of the polymer chain to undergo a transition from a rigid, glassy state to a compliant, rubbery state, which reversibly activates diffusion of encapsulated payload out of the particles. Therefore, the effect of the localized heating of the polymer matrix, in combination with the polymer $T_g$ depression by water, can be readily applied to precisely control the release of encapsulated contents from polymer microparticles. This release mechanism can be applied to a large number of polymer systems with no inherent light sensitivity, such as liposomes and nanogels.

Figure 4A:
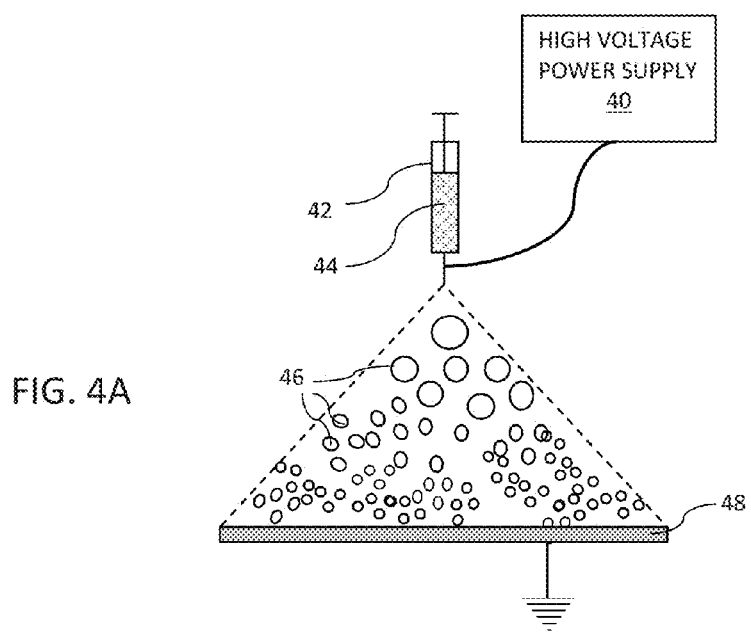
FIG. 4A is a schematic of an exemplary electrospray set-up for forming the nanoparticles.

In an exemplary embodiment, PLGA polymer capsules incorporating model release compounds were manufactured by electrospray, a formulation method that employs high voltages to inject charge into a liquid, causing the liquid to break into a jet of fine aerosol micro droplets propelled towards a metal plate collector. FIG. 4A provides a schematic of a basic electrospray system that may be used for forming the nanoparticles. Briefly, high voltage from voltage source 40 is applied to the metallic nozzle of a syringe 42 containing the polymer solution 44, causing the liquid to become charged as injected toward the collector 48. As the solvent evaporates in flight, dense, solid polymer microparticles 46 are generated. A variety of parameters, such as applied voltage, solution injection rate, and plate collector height, can be tuned to control the size and morphology of the particles produced. Furthermore, active molecules, such as the fluorescent dye, fluorescein, may be encapsulated by dissolving the compound in the polymer solution before electrospraying. This polyvalent method yields highly reproducible particles entrapping payloads with high encapsulation efficiencies. Additional details for procedures for using electrospray to form PLGA particles is described by Almeria B, et al. "*Controlling the morphology of electrospray-generated PLGA microparticles for drug delivery*", *Journal of colloid and interface science* (2010) 343(1):125-133.

Figure 4B:
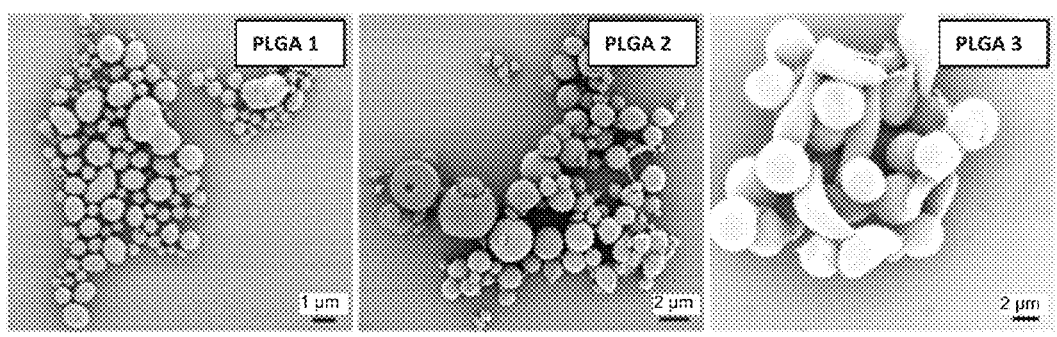
FIG. 4B is a set of SEM images of nanoparticles formed via electrospray of three different molecular weight PLGA solutions.

For testing, three different molecular weight PLGA solutions were used: PLGA 1 (ratio: 50:50; Mw: 7-17 kDa; alkyl ester terminated; Aldrich); PLGA 2 (ratio: 50:50; Mw: 24-38 kDa; alkyl ester terminated; Aldrich); and PLGA 3 (ratio: 50:50; Mw: 54-69 kDa; alkyl ester terminated; Aldrich). The size of the resulting particles is proportional to the polymer chain length, as shown in the SEM micrographs of FIG. 4B, which shows the different particles PLGA 1, PLGA 2, and PLGA 3 from left to right. Spherical particles were produced from PLGA 1 and PLGA 2 with average diameters of 0.5±0.1 μm and 2±1 μm respectively. For PLGA 3, both spherical (3.5±0.5 μm) and elongated particles (width=2.1±0.4 μm, length=10±2 μm) were obtained.

PLGA particles doped with fluorescein (free acid, 95% Aldrich) or retinoic acid were obtained as follows. PLGA (100 mg) was dissolved in 0.75 mL of chloroform ($CHCl_3$, 99.8%, EMD) and diluted with a solution containing the active compound in DMF (dimethylformamide, 99%, Aldrich) (Fluorescein (free acid, 95%, Aldrich): 40 mg/mL, 0.25 mL; Paclitaxel: 4 mg/mL, 0.25 mL) at 10% w/v. PLGA 1 solution was electrosprayed as is, but PLGA 2 and 3 solutions were further diluted to 5 and 2.5% respectively to prevent the formation of concomitant nanofibers. The polymer solutions were electrosprayed at 20 kV (Gamma High Voltage, ES30) at a flow rate of 0.5 mL/hr (KD Scientific) using a 25 gauge needle. The duration was adjusted between PLGA samples in order to yield the same final electrosprayed mass of polymer. Samples were collected onto microscope glass slides on an aluminum plate collector at a distance of 20 cm. The particles (~2 mg/slide) were removed from their glass slide substrate by sonication in phosphate buffered saline (PBS, 20×, pH 7.4, Cellgro), washed with PBS and finally dispersed in 5 mL of PBS.

Figure 5A:
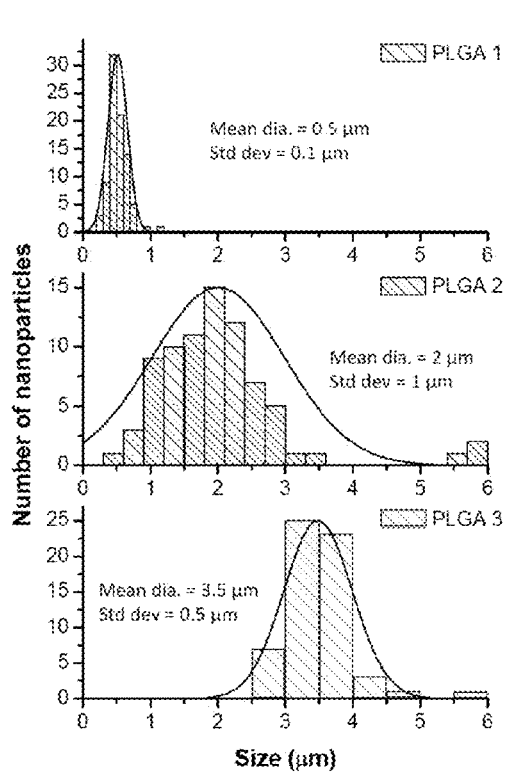
FIG. 5A is a histogram showing the size distribution of spherical fluorescein-loaded PLGA 1, PLGA 2, and PLGA 3 particles.
Figure 5B:
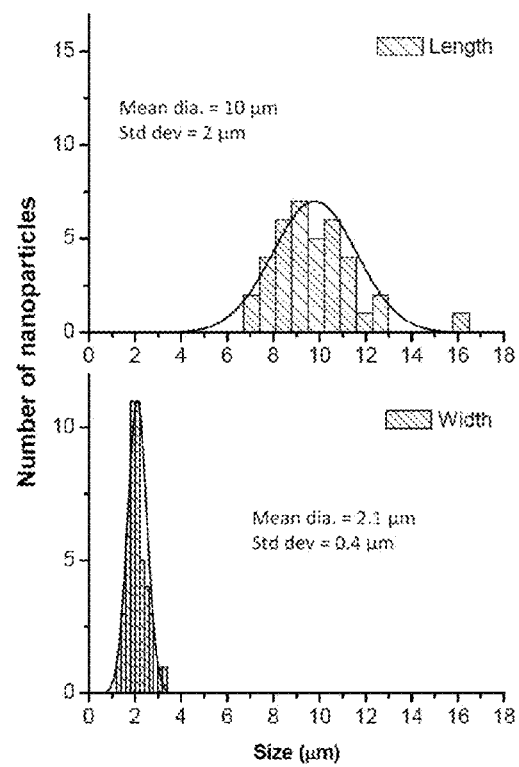
FIG. 5B is a histogram showing the size distribution of elongated fluorescein-loaded PLGA 3 particles.

The morphology of the polymer microparticles was examined by fluorescence microscopy (NIKON® ECLIPSE® with NIS-ELEMENTS® software) and SEM (Agilent, 8500). Particle diameter distributions were extracted from recorded fluorescence images and SEM photographs using NIKON® NIS-ELEMENTS® software and ImageJ software (NIH). The corresponding size distribution histograms are shown in FIGS. 5A and 5B. The amount of fluorescein incorporated into the various particles samples was determined by dissolving the particles with $CHCl_3$, releasing the dye molecules in the aqueous environment. Typically, 1 mL of $CHCl_3$ was added to 5 mL of microparticles suspension, vortexed for 5 min and diluted with deionized water to a final volume of 50 mL. The fluorescence of the mixtures was measured and the dye concentration quantified by linear calibration with matrix-matched aqueous standards.

Figure 5C:
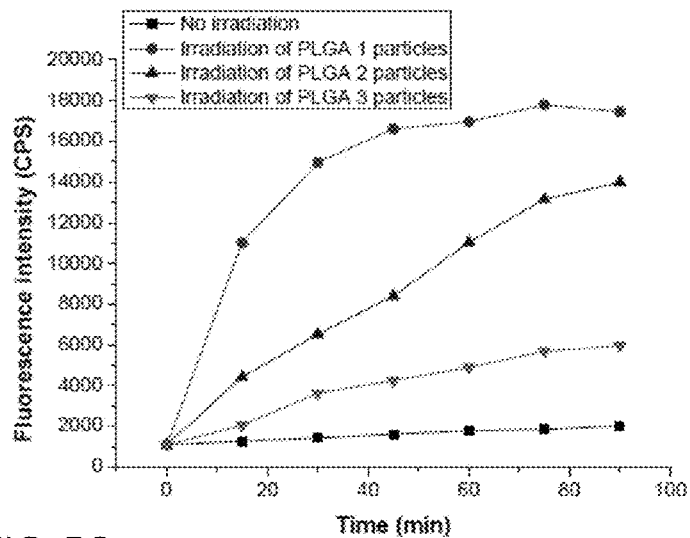
FIG. 5C is a plot of release rates for different size particles during irradiation.

Particle size may affect kinetics through the distance required for the payload to diffuse out in the aqueous environment. The effect of particle size and $T_g$ on release kinetics via NIR-induced heating was examined by comparing release of fluorescein from particles of different diameters produced from PLGA 1, PLGA 2 and PLGA 3. As shown in FIG. 5C, smaller particles with the lower $T_g$ released their payload more rapidly than larger particles with higher $T_g$ (values of 42, 52 and 54° C.) for PLGA 1, PLGA 2 and PLGA 3, respectively), which can be attributed to the larger surface-area-to-volume ratio of the smaller particles, the lesser tortuous path necessary to diffuse out of the particles, as well as the lower energy requirement for thermal plasticization.

Steady-state fluorescence measurements were performed using a FLUOROLOG® spectrofluorimeter (Horiba Jobin-Yvon) and quartz cuvette (volume: 1.5 mL, optical path length: 1.0 cm). Fluorescein was excited at 480 nm and measured at 520 nm. The amount of paclitaxel incorporated into the particles was determined by LC-MS (Agilent 1260 series with QUADRUPOLE™ 6120) after dissolution of the particles with $CHCl_3$.

Optical epifluorescence micrographs of fluorescein-loaded PLGA particles showed good encapsulation efficiency with no evidence of dye leaking. Fluorimetry confirmed high fluorescein encapsulation efficiency for all formulations, which corresponds to a loading capacity of ~8% w/w. High drug content facilitates water penetration in the system and leads to the creation of more porous polymer networks, which is highly desirable since it increases responsiveness to NIR induced thermal heating.

The swelling behavior of PLGA and its capacity to take up water are also correlated with its crystallinity, which depends on the molar ratio of the individual monomer components (lactide versus glycolide) in the copolymer chain. Lactic acid is more hydrophobic than glycolic acid and therefore glycolide-rich PLGA copolymers absorb more water. PLGA 1, PLGA 2 and PLGA 3 have lactide:glycolide ratios of 50:50, 75:25 and 85:15 respectively. Because of its higher hydrophilicity, PLGA 1 exhibits the highest water content and therefore should be most sensitive to NIR irradiation.

Example 1: Light-Induced Release

To determine whether low-power could induce sufficient local heating of water confined within PLGA 1 particles to allow release, solutions of particles in PBS pH 7.4 were irradiated with 980 nm light pulses (1 W).

Release from polymer particles was photo-initiated by irradiating a 250 μL aliquot (0.4 mg/mL) in a micro quartz cuvette at 980, 900 or 800 nm for specified periods of time using either a Ti: Sapphire laser (Mai Tai H P, Spectra Physics, 100 fs pulse width, 80 MHz repetition rate, 1 W) or a CW laser diode (Thorlabs, 980 nm only, 170-350 mW). A wave plate/polarizer combination was used to ensure an equal output power at 980, 900 and 800 nm. Release of fluorescein was followed by fluorescence spectroscopy and an emission spectrum was recorded immediately after every irradiation period, whereas paclitaxel release was followed by LC-MS. The morphology of the irradiated particles was investigated by optical microscopy and SEM. Solution temperatures were measured using a thin wire thermocouple (J-Kem Scientific) immersed in the particle solutions while irradiating with the NIR light sources and connected to a temperature controller (J-Kem Scientific). Digital photographs were acquired using a Panasonic DMC-ZS5.

Fluorescein release can be followed over time with the naked eye as the PBS solution changes from colorless to bright green. Epifluorescence microscopic observation further confirmed NIR-triggered release—before NIR irradiation, fluorescein was clearly loaded inside PLGA 1 particles, while after irradiation, fluorescence appeared as irregularly shaped dried patterns, rather than well-defined nanodomains. Interestingly, SEM images of irradiated particles (FIG. 4) showed no sign of change in particle morphology (i.e., size, shape, surface texture). Even after 90 minutes of 980 nm pulsed irradiation at 1 W, no degradation was observed. These observations indicate that photothermal heating of confined water, rather than other possible mechanisms such as optical cavitation, induces release of the encapsulated payload without disruption of the polymer matrix. Optical cavitation, or the formation of bubbles of vaporized gas in response to light, results from aqueous absorption of short laser pulses which generate a dielectric breakdown at the focal point, creating a plasma that expands and produces an acoustic shockwave. Since laser-induced cavitation requires intense laser light (>200 nJ/pulse) focused at a spot size of 0.5-5 μm (42), and only laser beams with pulse energy ≤60 nJ and spot size diameters ≥2 mm were used in this study, it is unlikely that the observed photo-release resulted from optical cavitation. Although no clear evidence of particle deformation was observed by SEM, irradiation did appear to reduce particle stability reflected by collapse and agglomeration. Aggregation could result from the particles being heated above their glass transition ($T_g$) and reaching a more rubbery state. Nonetheless, the temperature increase of the bulk solution was less than a few degrees above ambient. The temperature elevations of the bulk solution appeared to be dependent on laser power and sample volume. Irradiation at 980 nm (1 W, 15 min) of 0.25 mL, 1 mL, and 2 mL aliquots of a particle suspension resulted in maximum temperature elevations of approximately 10° C., 5° C., and 2° C., respectively. In order to avoid unnecessary variability in the release experiments due to bulk heating, temperature elevation was minimized by working with large sample volumes.

The rate of light-induced release of fluorescein from the particles was monitored by fluorescence spectroscopy. Fluorescein's emission from the particle suspension increased upon release because it fluoresces more intensely in polar environments and, like most organic dyes, self-quenches when its relative concentration exceeds ~$10^{-3}$ M, such as when it is entrapped within the PLGA particles (0.2 mol of fluorescein per kg of PLGA).

Figure 6A:
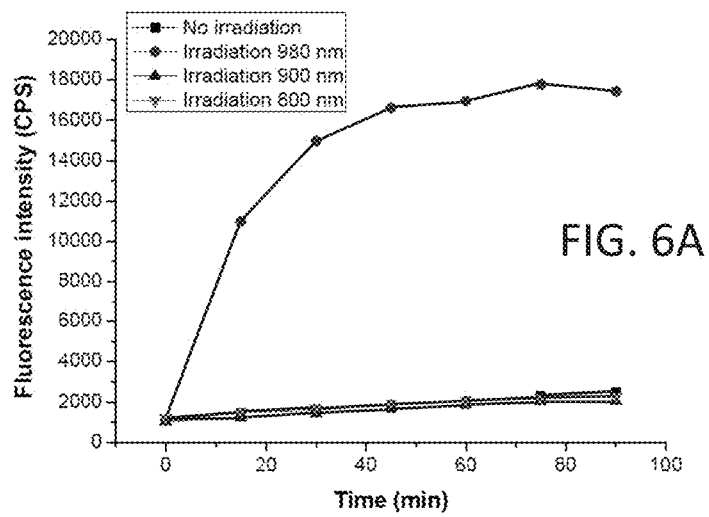
FIG. 6A is a plot of NIR-induced release with time at different laser wavelengths.
Figure 6B:
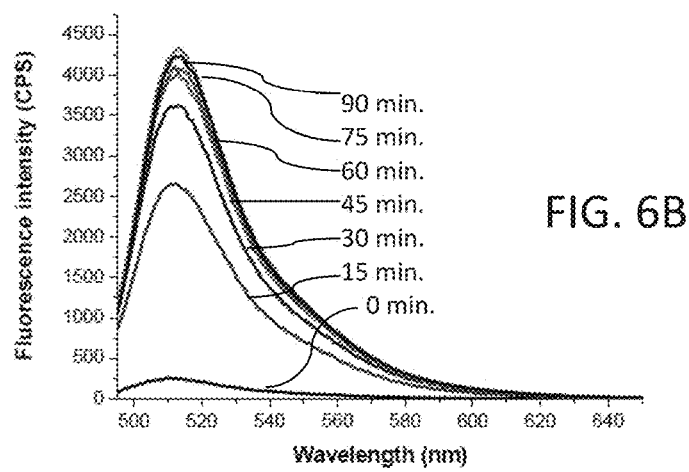
FIGS. 6B and 6C are plots of the fluorescence emission spectra taken every 15 min of (6B) unirradiated and (6C) irradiatied fluorescein-loaded PLGA 1 particles.
Figure 6C:
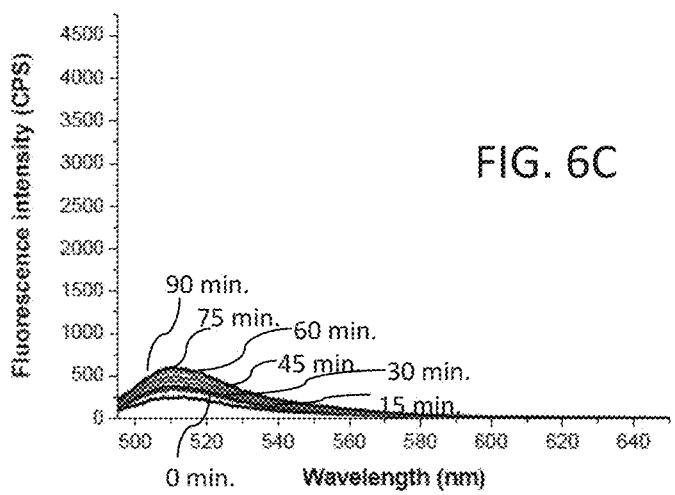

FIG. 6A plots the fluorescence intensity of fluorescein from PLGA 1 particles measured at 520 nm ($\lambda_{ex}$=480 nm) after 15 min irradiation increments with pulsed laser light (1 W) at 980 nm (circles), 900 nm (blue triangles), and 800 nm (inverse triangles). When excited at 980 nm (1 W), fluorescence intensity rapidly increases in the first 30 min, indicating a fast release of the dye from PLGA 1 particles into the polar medium (FIG. 6A, upper curve with circles; see also FIG. 6B for emission spectra (excitation wavelength=480 nm)) and saturates at around 60 min ($I/I_0$=16). In contrast, particles not exposed to light (off-state) or irradiated at 900 or 800 nm exhibit only a very slight increase of fluorescence ($I/I_0$=2) over the course of several hours (FIG. 6A, lower curves; see also FIG. 6C for emission spectra). This wavelength selectivity shows the energy absorbed by the PLGA particles is sufficient to induce heating and subsequent release of the payload only when resonant photon interactions are high, i.e., at 980 nm irradiation. Also, low background leakage suggests that the fluorescein molecules remain well-encapsulated inside the PLGA particles in the absence of irradiation. A 25-fold increase in rate of fluorescein release upon exposure with 980-nm NIR light (on/off ratio) was calculated. Since fluorescence intensity is proportional to the laser light exposure time, the quantity of released material is thus proportional to the amount of energy (number of photons) provided to the system.

Example 2: Role of Water in Payload Release

Figure 7A:
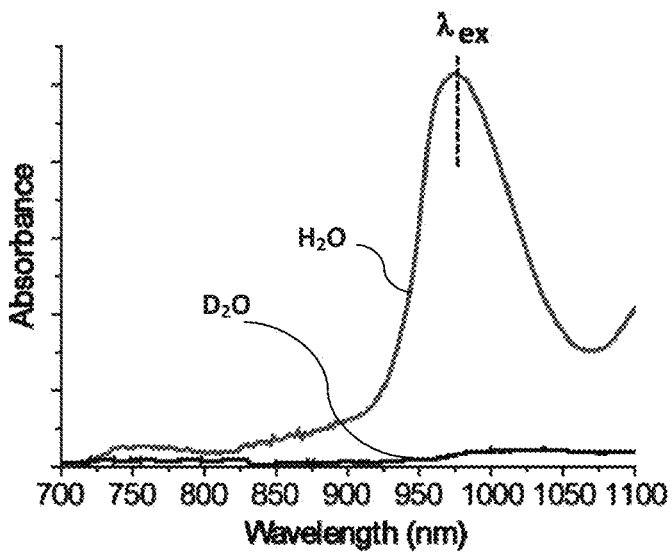
FIG. 7A is a plot of the absorption spectrum of deionized ($H_2O$) and deuterated water ($D_2O$)
Figure 7B:
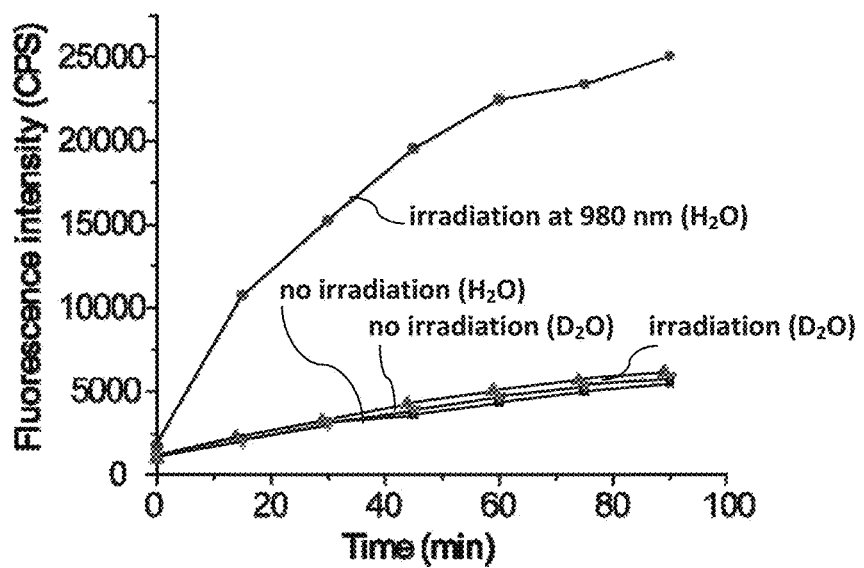
FIG. 7B shows the fluorescence intensity of fluorescein versus 980-nm pulsed laser exposure time for PLGA 1 particles dispersed in $H_2O$ and $D_2O$.

Entrapped water appears to play an important role in payload release by lowering the polymer glass transition temperature as well as absorbing the NIR light to induce localized heating inside the microparticles to facilitate release. To test this hypothesis, fluorescein release from PLGA microparticles was evaluated in deuterated water. The test procedures were the same as described above in Example 1. FIG. 7A provides a comparison of the absorption spectra of water and $D_2O$, showing that $D_2O$ (lower curve) does not absorb significantly at 980 nm. All of its corresponding vibrational transitions are shifted to lower energy by the increase in isotope mass and the vibrational band of $H_2O$ at 980 nm is therefore shifted to 1300 nm. In deuterated water, light-induced release of fluorophore molecules could only be the result of photonic absorption by the polymer nanostructures. For fluorescein-loaded microparticles suspended in $D_2O$, there was no sign of light-triggered release; the kinetic profiles matched those of a non-irradiated sample shown in FIG. 7B. This is consistent with prior results showing that the laser photonic densities (≤1 W) used in this study do not result in changes to PLGA particle morphology, and supports the conclusion that release requires strong absorbance of NIR by water.

Figure 8:
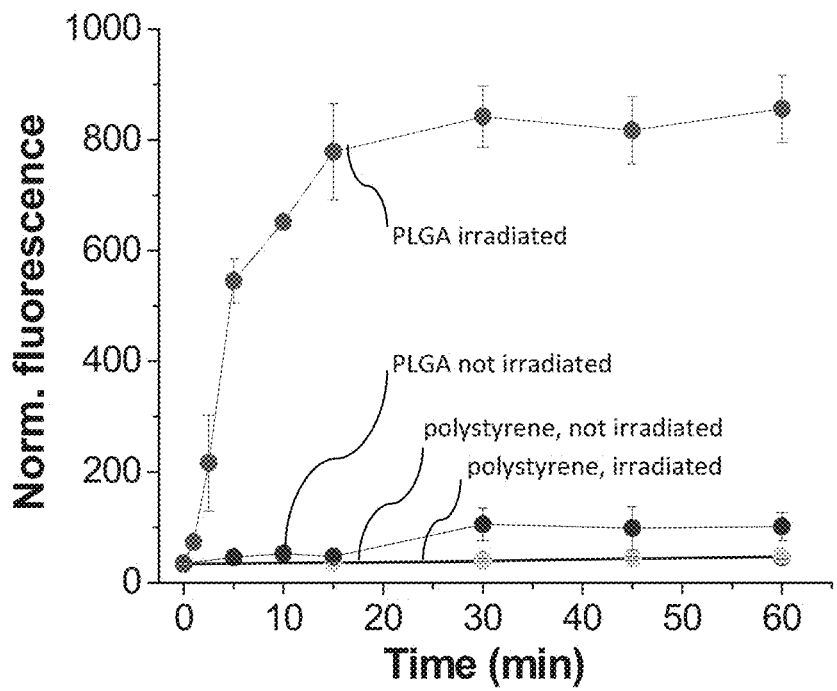
FIG. 8 is a plot of fluorescence (normalized) with time for PLGA and polystyrene, irradiated and unirradiated.

To further test the hypothesis, fluorescein was encapsulated in the hydrophobic polymer polystyrene (PS) and irradiated with 980 nm light to investigate payload release. The PS particles were confirmed to encapsulate the same amount of fluorescein as the PLGA particles. As shown in FIG. 8, no significant release from PS particles was observed, regardless of whether 980 nm radiation was applied. These results correlate well with the proposed scheme and demonstrate the role of water in this release mechanism.

Figure 9:
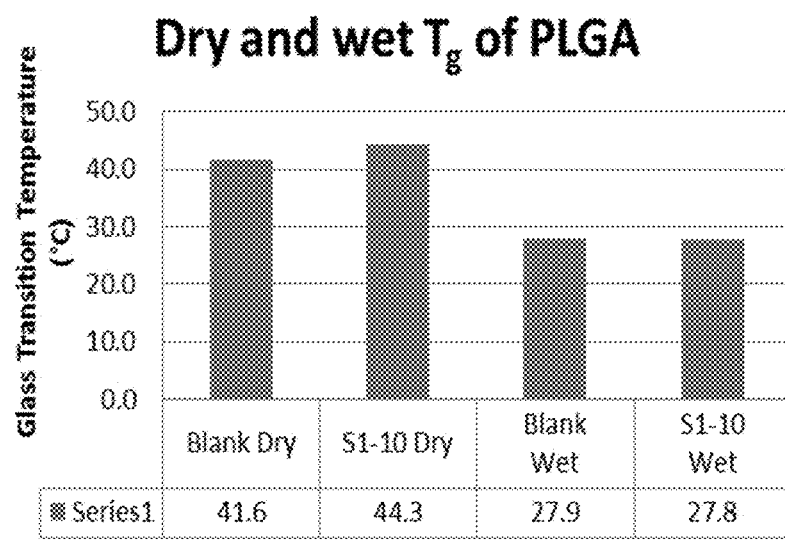
FIG. 9 is a comparison of the glass transition temperature $T_g$ of wet and dry PLGA measured using differential scanning calorimetry.

The role of water appears to be two-fold: water in the microparticles plasticize the polymer to lower its $T_g$, and is also responsible for the localized heating of the polymer to a temperature above its wet $T_g$. It has been shown in the literature that water and encapsulated small molecules can have an effect on the $T_g$ of a polymer (see, e.g., Tsavalas J G & Sundberg D C (2010), "Hydroplasticization of Polymers: Model Predictions and Application to Emulsion Polymers", *Langmuir* 26(10):6960-6966). Using Differential Scanning calorimetry (DSC) the dry and wet $T_g$ of PLGA microparticles were measured, with and without encapsulated fluorescein. FIG. 9 shows the results of this comparison, which led to the observation that encapsulating fluorescein had the effect of increasing the dry $T_g$ of the polymer slightly, but seemed to have no effect of the wet $T_g$ of PLGA, likely due to its strong burst release in solution and elimination of some of the payload initially entrapped within the particle. Additionally, a model proposed by Tsavalas et. al (supra) was used to calculate a wet $T_g$ value of 27.1° C., based on the measured dry $T_g$ value of 41.6° C. This calculated value was in very close agreement with the experimentally measured wet $T_g$ value from DSC measurements—indicated the presence of a saturated water environment induced a depression of the $T_g$ of PLGA particles from 42.6° C. to 27.9° C., thus confirming the presence of water inside the capsules. This was used to calculate a 5% water content weight fraction in the particles.

PLGA carriers are complex 3D systems made of interconnecting pores and channels of different size and tortuosity distributed throughout the entire volume of the spheres in which water can penetrate rapidly. Pre-existent pores (in contrast to dynamically-formed pores created upon degradation) found in PLGA particles of similar composition and size present diameters between 3-20 nm. Since the size and shape of the water domains are intimately linked with the pore size, it appears that the confined water also adopts a similar cylindrical morphology The depressed $T_g$ induced by water is an important aspect of this release-mechanism since significant heating of the system is undesirable. DSC results suggest that the local temperature inside the particles must be at least as high as the measured wet $T_g$ of the polymer in order for release to be observed.

Example 3: Evaluation of Internal Particle Temperature

Fluorescent molecular thermometer represents a promising tool for intra-particle thermometry, as it functions at the molecular level and, thus, would be effective in monitoring temperature within micron-sized domains. The strong effect of temperature on the fluorescence properties of molecular probes has been known for quite some time and has led to various sensing schemes most often based on changes in emission wavelengths and/or fluorescence intensity. In addition, excited-state lifetimes of fluorescent molecules are intensely affected by temperature, showing, in most cases, shorter lifetimes at higher temperatures. This temperature dependence is largely due to changes in non-radiative decay rates, for which their importance increases at higher temperatures. In this study, FLIM was used to extract intra-particle temperature mapping by means of fluorescein lifetime as the temperature-dependent variable. With this thermometric methodology, temperature measurements can be made inside polymeric particles with high spatial and temperature resolution, which unequivocally revealed increases in temperature upon irradiation at 980 nm.

To probe individual particles for an extended period of time, the particles were stabilized in acrylamide hydrogels. The hydrogels containing the particles were obtained by mixing a 250-μL particles aliquot (0.4 mg/mL) with acrylamide (60 mg), bis-acrylamide (1.4 mg) and lithium acylphosphinate salt (58 mg/mL, 10 μL). The gelation was photo-initiated under UV irradiation (30 sec, Luzchem). To obtain the free dye embedded in hydrogels, 250-μL fluorescein-doped PLGA particles aliquot (0.4 mg/mL) was first heated at 65° C. for 15 min to release the dye molecules from the PLGA particles and the empty polymer particles were removed by centrifugation before applying the same gelling process.

Fluorescence lifetime spectroscopy was done using a time-correlated single photon counting (TCSPC) system (Horiba) equipped with a NanoLED excitation source (488 nm, 1 MHz impulse repetition rate, Horiba) and a R928P detector (Hamamatsu Photonics, Japan). The detector was set to 520 nm for detection of fluorescein. The slit width varied between 2 and 20 nm to achieve an appropriate count rate. The instrument response function (IRF) was obtained by using a scattering solution of Ludox-40 (Sigma-Aldrich) in water (prompt) at 480 nm emission. The samples and the prompt were measured in a semi-micro quartz cuvette. The lifetime was recorded on a 450 ns scale. A total of 4094 channels were used with a time calibration of 0.110 channel/ns. All decay curves were fitted with one exponential. The fluorescence lifetimes were extracted using DAS6 v6.6 decay analysis software (Horiba). The goodness of fit was judged by $\chi^2$ values, Durbin-Watson parameters, and visual observation of the fit line and residuals, which should be distributed randomly about zero.

Fluorescence lifetime imaging was performed on a SliceScope two-photon microscope (Scientifica, UK) using a 60× water immersion objective (LUMPLFLN 60×W, NA=1.0, Olympus). A Chameleon Ultra II IR laser (Coherent) (80 MHz repetition rate, 100-150 fs pulses) tuned at 980 nm was used for the excitation of both fluorescein and confined water. ScanImage r3.8 was used to control the scanning mirrors (50). Fluorescence emission was detected with a hybrid PMT detector (HPM-100-40, Becker and Hickl, Germany) between 490-540 nm by means of a GFP emission filter (ET 515/50, Chroma). The acquisition of fluorescence lifetimes was synchronized by a TCSPC module (SPC-150, Becker and Hickl). The following parameters were kept constant for all acquired images: pixel size (30 nm; all 512×512 pixels), pixel dwell time (3.2 μs), laser excitation intensity (10 mW after the microscope objective), and FLIM acquisition time (60 seconds/image). Fluorescence lifetime images were analyzed with SPCimage (Becker and Hickl). To minimize lifetime calculation errors, we used a minimum threshold of 15 photons at the peak (corresponding to ~1000 photons per pixel), and a binning factor between 2 and 10 pixels to assure sufficient photons in the regions of interest. The same calculated IRF was used for all experiments. The control images of free fluorescein in polyacrylamide gels were analyzed with a single exponential model, whereas the PLGA particles images were much better fitted with a double exponential model. The goodness of fit was evaluated with $\chi^2$ values and visual observation of the fit line and residuals.

Figure 15A:
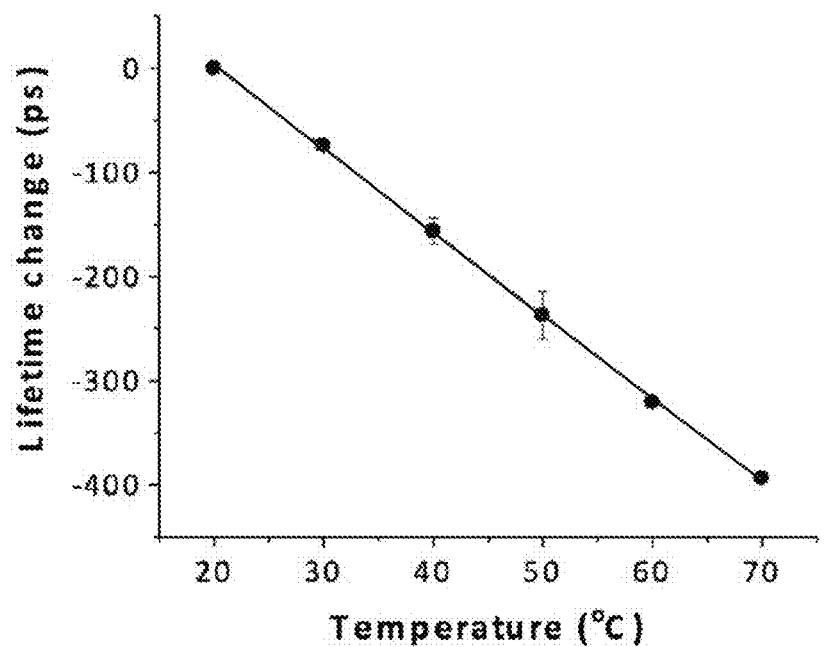
FIGS. 15A and 15B are plots of average free fluorescence lifetime in acrylamide gel heated to different temperatures and changes in average free fluorescence lifetime upon NIR radiation for different time periods.
Figure 15B:
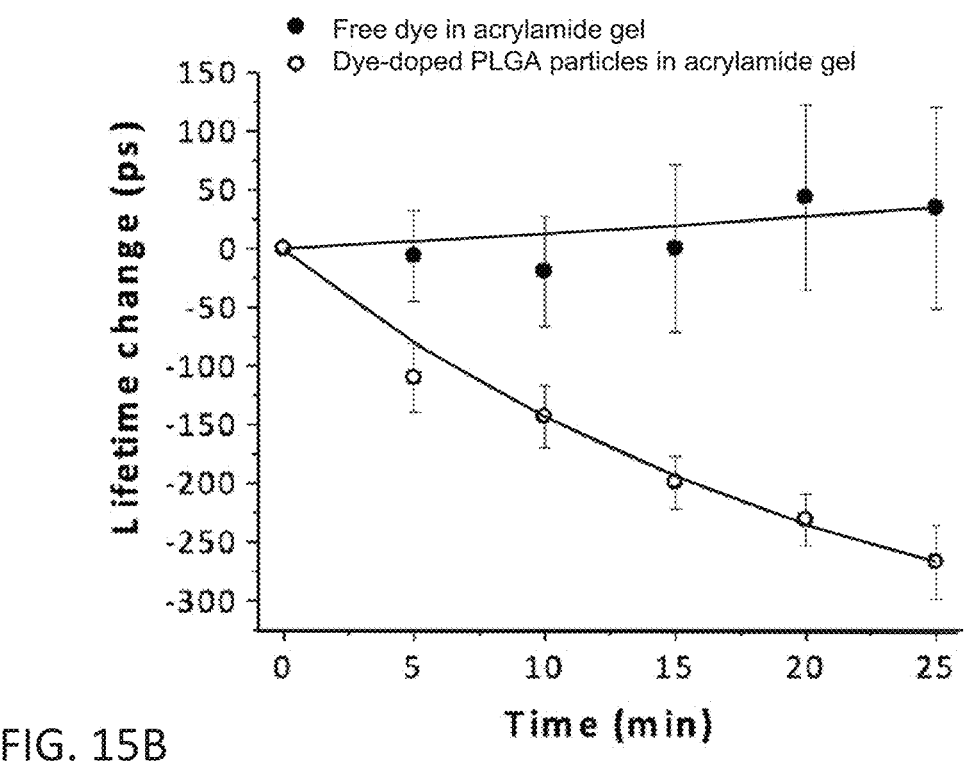

The relationship between free fluorescein lifetime and temperature was used as a calibration curve for temperature imaging. This was achieved by manually heating an acrylamide gel containing fluorescein molecules from 20° C. (room temperature) to 70° C. and acquiring lifetime decay curves using a TCSPC system on a spectrofluorometer. The average excited-state decay times ($\tau_{av.}$) were then extracted from the decay curves and plotted as lifetime change ($\Delta\tau_{av.}=\tau_{av.}(X\ °C.)-\tau_{av.}(20°C.)$) as a function of temperature (FIG. 15A). The excited-state lifetime deceased with increasing temperature following a negative linear relationship with a calculated sensitivity of −8 picoseconds/° C. For the FLIM measurements, gels containing fluorescein-doped PLGA particles were placed in a reading chamber containing water. Single particles or small particle aggregates were subjected to continuous irradiation at 980 nm (10 mW) in a raster scan motion to ensure complete irradiation of the entire particle/aggregate. FLIM images were acquired every 5 min and an average lifetime was extracted from each image by integration of all pixels. Since fluorescein can be excited at 980 nm through two-photon absorption, the decay curves could be acquired with a single laser beam set-up, while we stimulated confined water heating. The average lifetime of fluorescein within the particles, extracted from FLIM images and plotted as lifetime change versus irradiation time (FIG. 15B, open circles), reveals a clear decrease in lifetime ($\Delta\tau_{av.}=-267$ ps, $t_{irr.}=25$ min) following an exponential trend. According to the change in lifetime versus temperature calibration curve shown in FIG. 15A, an average internal temperature of 34, 45 and 54° C. was reached following 5, 15 and 25 min irradiation, respectively; temperatures well above the wet $T_g$ of the dye-doped PLGA particles. On the other hand, free fluorescein embedded in acrylamide gels did not present a similar irradiation-induced decrease in lifetime (FIG. 15B, solid circles). This data suggests that the absorbed optical energy can be efficiently dissipated throughout the whole bulk hydrogel, which prevents localized heating. Upon irradiation at 980 nm, the internal temperature increases, which corresponds to a decrease in lifetime. Even though the dye-doped particles present different average lifetime values before irradiation (likely due to variations in particle size and dye loading), the change in lifetime of each particle as a function of irradiation time is comparable regardless of its initial value. Observed fluorescence indicated that the thermal changes (decrease in lifetime) happen exclusively inside the particles; no noticeable changes in the hydrogel regions were observed. Furthermore, because of the high spatial resolution of the FLIM system, regions of intense changes in lifetime are discernible throughout the whole polymer matrix, which suggests that water-rich areas capable of generating substantial heat are present within the PLGA particles. The temperature changes are more modest than in other thermally induced release mechanisms, especially compared to those involving gold nanostructures, with temperature increases reported to be well above 250° C., which raises concerns about the stability of cargoes at such high temperatures.

The observed selective heating of the confined water versus the bulk aqueous environment is attributed to the enormous volume difference between the two. Since heat capacity is an extensive property, for the same amount of energy introduced into the system, nano-domains of water will be heated to significantly higher temperatures than their bulk water counterparts. However, the heating is mitigated due to the high surface area to volume ratio of the nanodroplets, as the excited confined water rapidly dissipates heat to the surrounding polymer matrix by conductive heat transfer. Furthermore, as the entire particle is heated up, convective heat transfer to the bulk water simultaneously removes heat from the surface of the particles. Nonetheless, since heat dissipation from the excited water droplets to the surrounding environment (polymer matrix, water) is much slower (microseconds) than the dynamics involved in vibrational absorption of photonic energy (picoseconds), electromagnetic energy can still accumulate inside the particles and elevate the temperature of the confined water domains when exposed to 980 nm laser irradiation. As previously noted, compared to metallic nanostructures, the maximum observed temperatures reached inside the particle are much smaller. Compared to gold, for example, water has a much higher heat capacity (Cp, water=4.186 J/g·° C.; Cp, gold=0.129 J/g·° C.) (44), which means that it requires more optical energy to raise its temperature by the same amount. Ultimately, with most biodegradable polymers having their $T_g$ below 60° C. (45), the resulting localized heating is enough to soften polymer matrices and induce release of the encapsulated payloads. An attractive option to increase the photon-to-heat conversion efficiency, and hence conserve the same release efficacy at lower laser powers, would be to exploit water absorption bands with greater absorptivity (i.e., 1200 nm, 1450 nm, 1950 nm) (43). This could prove especially useful for release experiments in highly scattering environments, as the laser beam would quickly broaden and lose its high peak power while travelling through the sample.

Example 4: Wavelength Selectivity

Figure 10A:
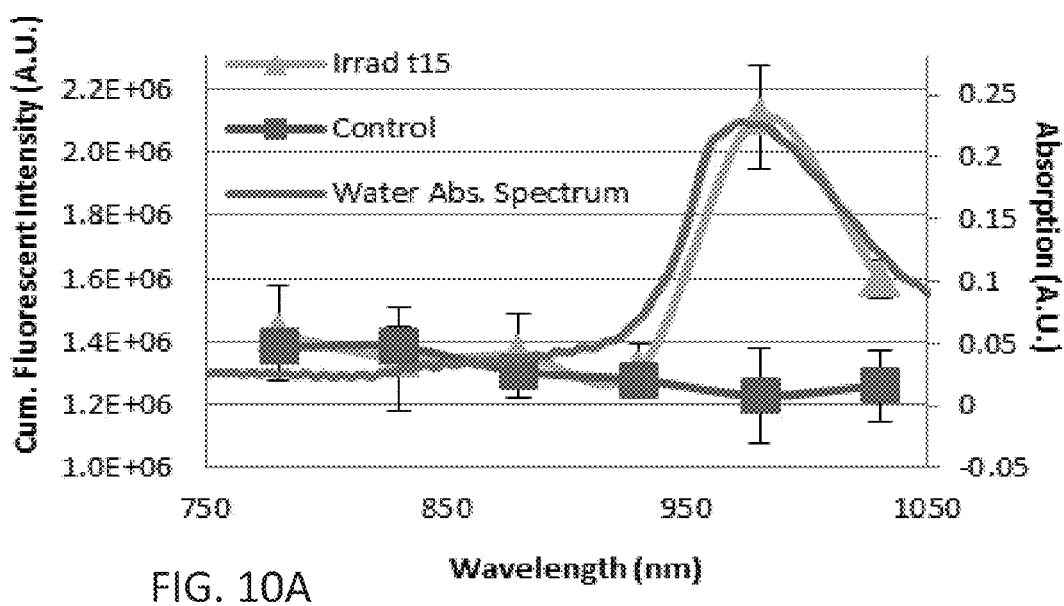
FIG. 10A is a plot of the cumulative fluorescence intensities after 15 min irradiation on the same graph as the absorption spectrum of water.
Figure 10B:
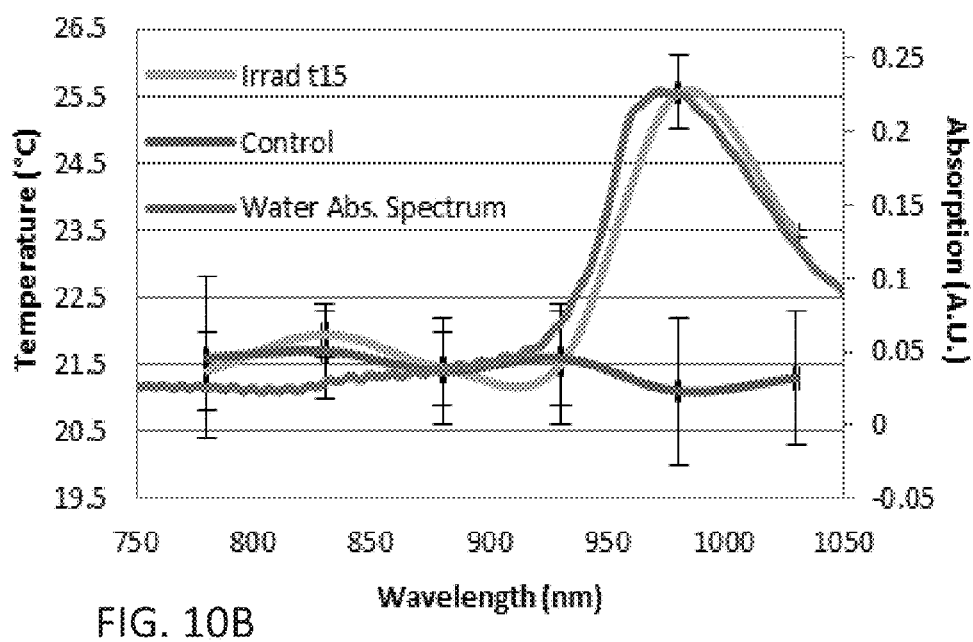
FIG. 10B is a plot of temperature of the bulk solution after irradiation.

The wavelength selectivity of the photo-thermal process was explored by monitoring fluorescent intensity and temperature of samples, before and after irradiation. Aliquots containing polymer microparticles were made by suspending particles in DI $H_2O$ at a concentration of 0.5 mg/mL and irradiating for 15 min at different wavelengths (50 nm increments, starting at 780 nm). The power was adjusted to 500 mW at each wavelength for consistency and the temperature was monitored. Fluorescence changes indicative of release were significantly higher when irradiating at wavelengths that coincided with the water absorption band around 980 nm. Profiles following irradiation at non-resonant wavelengths were similar to those for non-irradiated samples. FIG. 10A plots the cumulative intensities of the samples after 15 min irradiation on the same graph as the absorption spectrum of water. The overlap of the data strongly suggests the wavelength selectivity of the NIR radiation. Temperature of the bulk solution was also monitored (plotted in FIG. 10B) and found to be highest when irradiating at the maximum of the water absorption band (980 nm), again suggesting the wavelength selectivity of the 980 nm radiation.

Figure 11:
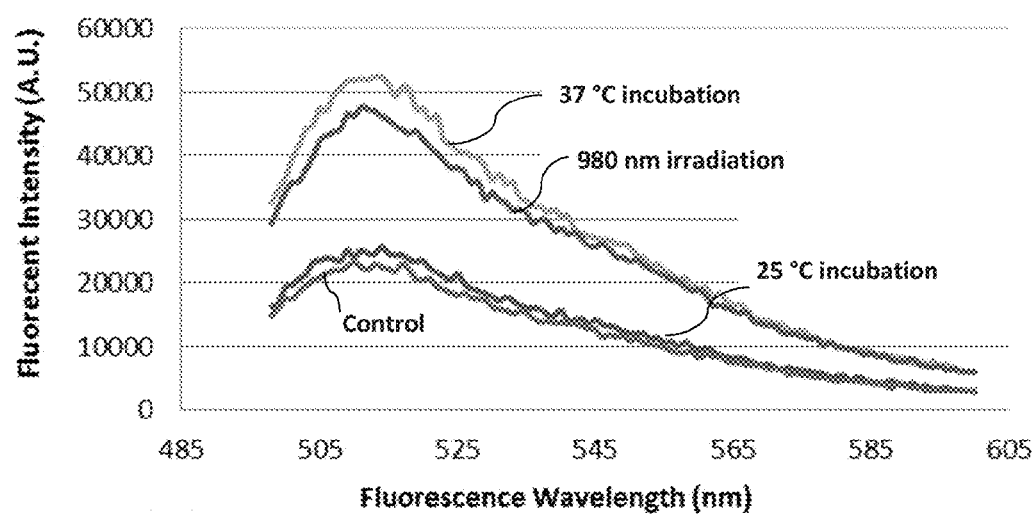
FIG. 11 is a plot of fluorescence intensity for irradiated and manual fluorescein-loaded polymers in solution.

While the result seems to suggest that the laser was successful in inducing release, a question arises as to whether the release was due to the heating of the bulk water. To confirm that the release of the payload was due to localized heating of confined water, and not due to heating of bulk water, 1 mL aliquots containing polymer particles were manually heated at 25° C. and 37° C. for 15 minutes and sample fluorescence measured. These measurements were compared to results gathered due to irradiation at 980 nm, Manual heating to 25° C. did not result in significant release compared to non-heated control samples, while manual heating to 37° C. resulted in release comparable to the release induced by irradiating at 980. This data, shown in FIG. 11, is in alignment with the measured wet $T_g$ of the polymer: manual heating to temperatures below the wet $T_g$ did not result in significant release of payload while manual heating to temperatures above the wet $T_g$ did. Furthermore, temperature elevations of the bulk solution were volume dependent, as one might expect. Irradiation of 0.25 mL, 1 mL, and 2 mL aliquots of water at 1 W, for 15 min, resulted in temperature elevations of approximately 10° C., 5° C., and 2° C., respectively. If these particles were to be applied in the body, which is essentially a large heat sink, the temperature elevation of the surrounding bulk environment should be negligible.

Figure 12A:
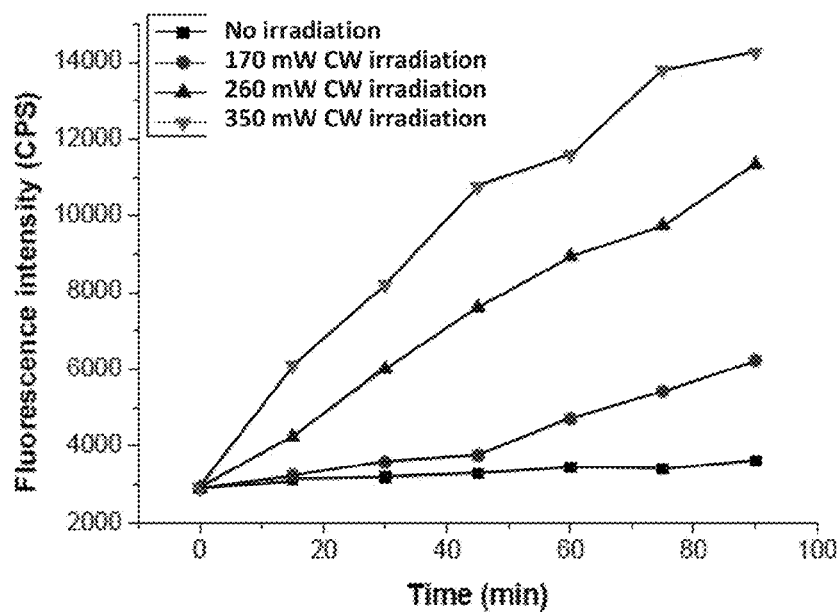
FIG. 12A is a plot of fluorescence intensity from fluorescein-loaded PLGA 1 particles measured at 520 nm ($\lambda_{ex}$=480 nm) after 15 min irradiation increments with 980 nm CW laser light at different power densities.
Figure 12B:
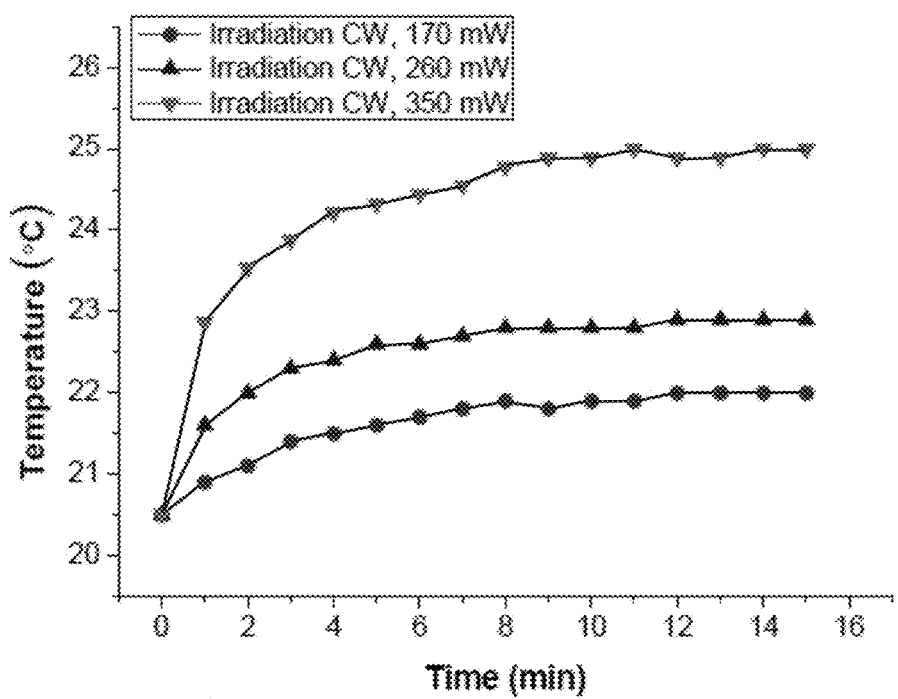
FIG. 12B plots temperature changes in aqueous solutions containing PLGA particles after exposure to CW laser exposure at different output powers.

The photophysical process of conversion to trigger the payload release occurs through the excitation of an overtone vibration absorptionhydrophoby, and so, does not necessitate delivery of 980 nm light as short, focused light pulses, in contrast to simultaneous two-photon absorption processes. Thus, efficient light-triggered release can also be achieved at low excitation powers using a more economical and biologically relevant continuous wave (CW) laser set-up. FIG. 12A is a plot of fluorescence intensity of fluorescein from PLGA 1 particles measured at 520 nm ($\lambda_{ex}$=480 nm) after 15 min irradiation increments with 980 nm CW laser light at different power densities. These results show that by varying the excitation power density from 170 mW to 350 mW, the rate of release depends on the average NIR photon energy used to excite PLGA particles. As expected, the release of fluorescein occurs more rapidly at higher CW power densities, with an on/off ratio of 18 when irradiating at 350 mW compared to 14 and 5 when irradiating at 260 and 170 mW, respectively. After 90 minutes, a cumulative 69, 52, and 20% of fluorescein was released from the PLGA particles at CW output powers of 350, 260, and 170 mW, respectively. After 90 min, a cumulative 69, 52, and 20% of fluorescein was released from the PLGA 1 particles at CW output powers of 350, 260, and 170 mW, respectively. FIG. 12B plots the temperature changes in aqueous solutions containing PLGA particles following exposure to CW laser exposure at output powers of 170, 260 and 350 mW.

These experiments show that the elevation of the sample's environmental temperature to temperatures above the $T_g$ of the polymer contributes to release, as accumulated energy in the bulk water can also be transferred to the polymer capsules. However significant, these temperature changes are considerably more modest than occur with other thermally-induced release mechanisms. For example, gold nanostructures have been reported to produce temperature changes ranging from 67° C. following 30 min irradiation at 1.1 W to boiling within 5 min at 1.5 W. The temperature increase around the metal particle when illuminated with NIR laser light around 800 nm has been shown to be well above 250° C. (11-12), limiting gold-based photothermal release to heat-stable cargo; the mechanism we report is applicable for a broader range of molecules. Another disadvantage of gold-based photothermal release is that extensive irradiation with high power NIR light causes irreversible damage to the metal NPs, which deteriorates their photothermal responsiveness over time.

Example 5: Reversibility of Release

Figure 13:
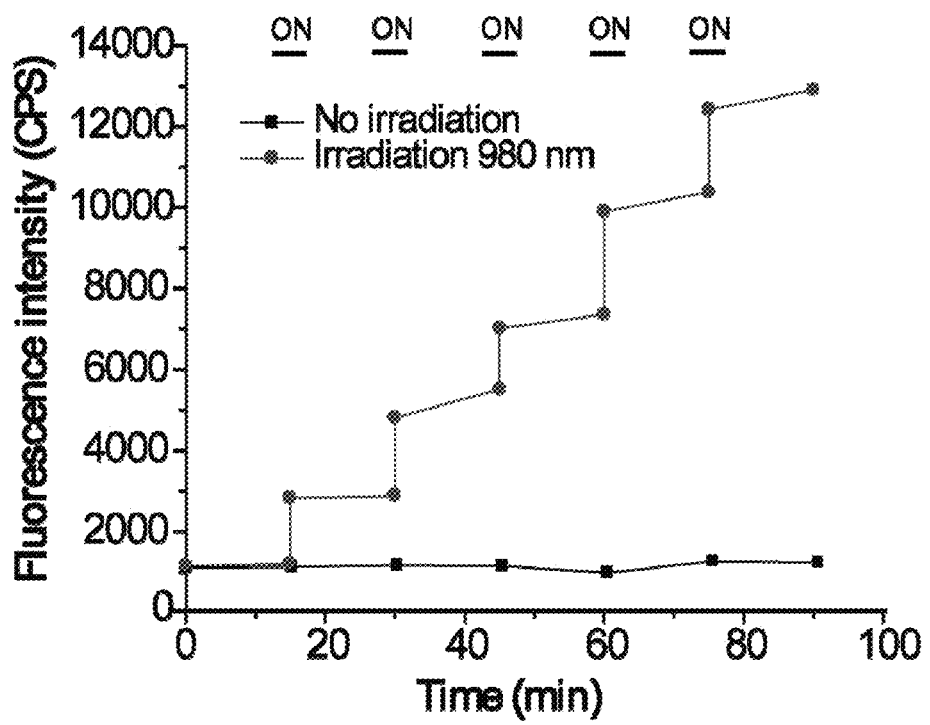
FIG. 13 is a plot of fluorescence intensity for stepwise triggered release from fluorescein-loaded PLGA 1 particles for a multiple OFF-ON cycles of 980 nm irradiation.

Since robust control of release is desired, it is important to test the reversibility of the release mechanism. A permanent effect would cause continued release after irradiation ends, while a reversible, on-demand effect would lead to slowed release profiles following termination of laser irradiation. To test reversibility, a fluorescein-doped PLGA 1 microsphere suspension was irradiated repeatedly using NIR light (pulsed laser, 980 nm, 1 W) for 5 min, followed by 15-min intervals during which the laser was turned off. The results are shown in FIG. 13, which is a plot of fluorescence measured during six cycles of off-state (15 min) and five cycles of on-state (15 min irradiation, 980 nm, pulsed laser, 1 W), A rapid increase in fluorescein release from the PLGA particles was observed upon NIR irradiation, but the release rate practically decreased to its initial rate when the NIR irradiation was switched off. A similar on/off release ratio was observed over multiple consecutive exposures. This stepwise triggered release experiment demonstrates the reversibility of this photochemical mechanism, indicating that the PLGA particles retain their integrity upon NIR irradiation. In this case, the small payload release observed within the off-state is believed to be attributed to water molecules diffusing into the void created by the loss of fluorescein from the particles, which in turn encourages diffusion out of the particles.

Example 6: Release Effect of Hydrophobicity

Figure 14A:
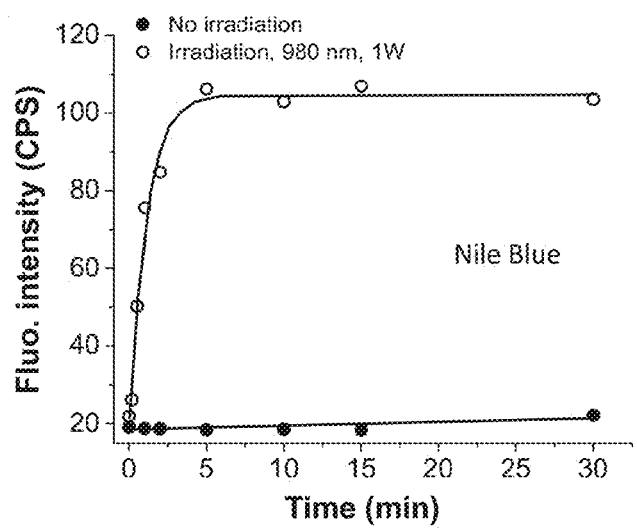
FIGS. 14A-14C are plots of fluorescence intensity after NIR irradiation of suspensions of Nile Blue-doped PLGA particles, Nile Red-doped PLGA particles, and IR780-doped PLGA particles, respectively.
Figure 14B:
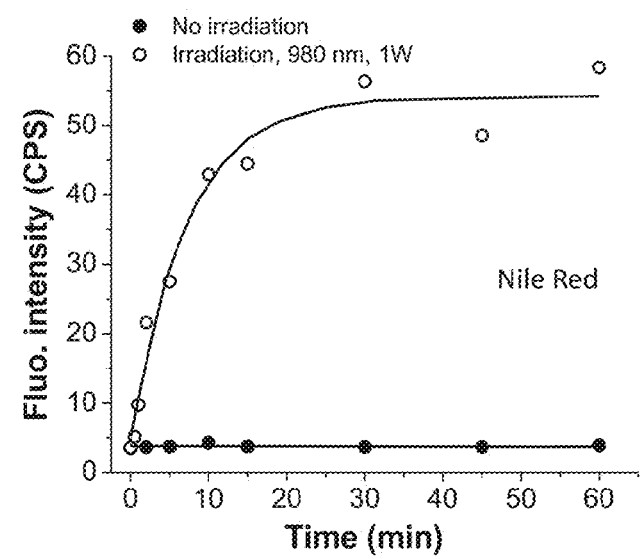
Figure 14C:
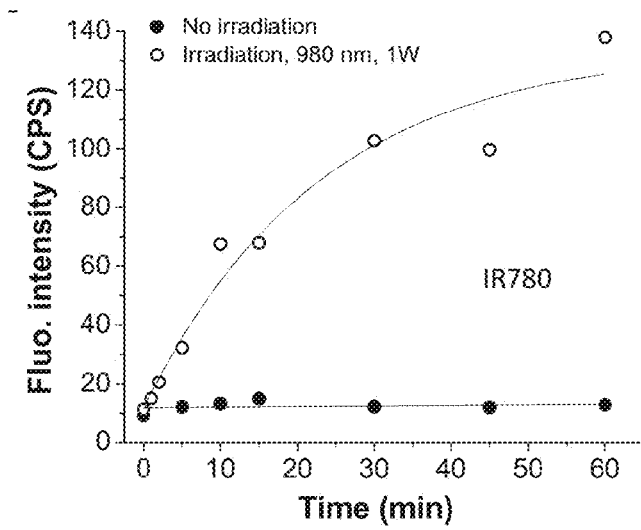

Since the PLGA capsules are capable of encapsulating both hydrophobic and hydrophilic compounds at high efficiency, the ability of this photo-thermal process to release small payloads of varying hydrophobicity was investigated. Using electrospray, IR780, nile red, and nile blue (in order of increasing polarity) were loaded into spherical PLGA capsules (~10% w/w) of 0.7±0.1 µm, 1.4±0.3 µm, and 1.2±0.4 µm in size, respectively. For all aqueous suspensions of dye-loaded PLGA particles, continuous NIR exposure (980 nm, pulsed laser, 1 W) resulted in continuous release of the dyes over time. The results are shown in FIG. 14 for nile blue ($\lambda_{ex}$=460 nm, $\lambda_{em}$=475-750 nm) (FIG. 14A), nile red ($\lambda_{ex}$=560 nm, $\lambda_{em}$=570-750 nm) (FIG. 14B) and IR780 ($\lambda_{ex}$=740 nm, $\lambda_{em}$=750-900) nm. (FIG. 14C). In each case, the control was no irradiation (solid circles).

These findings revealed that this photo-thermal process is capable of sustaining release of both hydrophilic and hydrophobic compounds. Interestingly, a noticeable trend in the kinetics of release related to differences in dye polarity could be observed, i.e., more polar dyes were released faster. This difference could result from variations in water absorption: Hydrophilic content facilitates water penetration in polymeric carriers and leads to the creation of more porous and swelled polymer networks, while more hydrophobic compounds hinder diffusion of water into the structure. Particles encapsulating hydrophilic cargos would then be more sensitive to NIR irradiation, and release their content more readily. Variations in release rate could also relate to the energy needed to induce diffusion out of the matrix, which should be lower for hydrophilic than hydrophobic compounds, since hydrophobic compounds would have higher affinity to the hydrophobic carrier.

The present invention provides a procedure for controlled release of a payload from polymer particles based upon heating of encapsulated water using 980 nm NIR light. The polymer particles, which have no inherent light sensitivity, contain encapsulated nanodroplets of water that can be selectively heated to transfer heat to the polymer matrix, elevating the internal temperature of the polymer particles and causing them to reach a more rubbery state, allowing diffusion of the payload out of the particles. Resonant photon interactions with water at 980 nm can induce significant release of both hydrophilic and hydrophobic molecules. The on-demand rate of release depends on the average NIR photon energy administered to the system and varies inversely with the size of the particles. Multiple consecutive NIR exposures can be used to obtain multiple release doses without irreversible rupture of the carriers, and, given the high encapsulation efficiency of the electrospraying technique, allows a large number of release cycles. This NIR-induced thermal plasticization-based release mechanism provides significant benefits over existing release strategies including wavelength selectivity and high sensitivity, low CW laser power requirements, avoids excessive heating. The present invention provides for the use of light-activated self-healing capsules, extracellular scaffolds (nanofibers, hydrogels) for on-demand delivery of cues for cell proliferation, differentiation, or migration, activatable fluorescent particles based on thermochromic dyes, as well as light-triggered drug delivery systems.

There are many useful applications for the present invention for on-demand delivery of small molecules to cells or within living organisms. The inventive delivery method could be commercialized by mass production of PLGA (or other widely available polymer) particles encapsulating pharmacological agents commonly used in cell biology, or as a new application of existing polymers, as polymer producing companies could provide formulation protocols. For example, well dispersed PLGA micro-particles encapsulating a therapeutic payload could be readily injected into the eye using a micro-needle. Typically, PLGA has a short retention time (2-3 months) inside the body due to degradation via breakage of ester bonds in the polymer backbone. However, if a laser were to be used to induce aggregation and/or clumping of the particles into a large drug reservoir, the retention time of the drug could be increased for longer-term (extended) release.

REFERENCES (INCORPORATED HEREIN BY REFERENCE)

1. Fomina N, Sankaranarayanan J, & Almutairi A (2012) Photochemical mechanisms of light-triggered release from nanocarriers. *Advanced Drug Delivery Reviews* 64(11):1005-1020.
2. Leung S J & Romanowski M (2012) Light-Activated Content Release from Liposomes. *Theranostics* 2(10): 1020-1036.
3. Esser-Kahn A P, Odom S A, Sottos N R, White S R, & Moore J S (2011) Triggered Release from Polymer Capsules. *Macromolecules* 44(14):5539-5553.
4. Johnston A P R, Such G K, & Caruso F (2010) Triggering Release of Encapsulated Cargo. *Angew Chem Int Edit* 49(15):2664-2666.
5. Timko B P, Dvir T, & Kohane D S (2010) Remotely Triggerable Drug Delivery Systems. *Advanced Materials* (Weinheim, Germany) 22(44):4925-4943.
6. Weissleder R (2001) A clearer vision for in vivo imaging. *Nature biotechnology* 19(4):316-317.
7. Hribar K C, Lee M H, Lee D, & Burdick J A (2011) Enhanced Release of Small Molecules from Near-Infrared Light Responsive Polymer-Nanorod Composites. *ACS Nano* 5(4):2948-2956.
8. Wu G, et al. (2008) Remotely Triggered Liposome Release by Near-Infrared Light Absorption via Hollow Gold Nanoshells. *Journal of the American Chemical Society* 130(26):8175-8177.
9. You J, Shao R, Wei X, Gupta S, & Li C (2010) Near-Infrared Light Triggers Release of Paclitaxel from Biodegradable Microspheres: photothermal Effect and Enhanced Antitumor Activity. *Small* 6(9):1022-1031.
10. Choi H S, et al. (2007) Renal clearance of quantum dots. *Nat. Biotechnol.* 25(10):1165-1170.
11. Wu G, Mikhailovsky A, Khant H A, & Zasadzinski J A (2009) Synthesis, characterization, and optical response of gold nanoshells used to trigger release from liposomes. *Methods in Enzymology* 464 (Liposomes, Part F):279-307.
12. Radt B, Smith T A, & Caruso F (2004) Optically addressable nanostructured capsules. *Advanced Materials* (*Weinheim, Germany*) 16(23-24): 2184-2189.
13. Fomina N, McFearin C, Sermsakdi M, Edigin O, & Almutairi A (2010) UV and Near-IR Triggered Release from Polymeric Nanoparticles. *Journal of the American Chemical Society* 132(28):9540-9542.
14. de Gracia Lux C, et al. (2012) Single UV or Near IR Triggering Event Leads to Polymer Degradation into Small Molecules. *ACS Macro Letters* 1(7):922-926.
15. Jochum F D & Theato P (2010) Thermo- and light responsive micellation of azobenzene containing block copolymers. *Chemical Communications* (Cambridge, United Kingdom) 46(36):6717-6719.
16. Lee H-i, et al. (2007) Light-induced reversible formation of polymeric micelles. *Angewandte Chemie, International Edition* 46(14):2453-2457.

17. Koester H J, Baur D, Uhl R, & Hell S W (1999) Ca2+ fluorescence imaging with pico- and femtosecond two-photon excitation: Signal and photodamage. *Biophys J* 77(4):2226-2236.
18. Konig K, Becker T W, Fischer P, Riemann I, & Halbhuber K J (1999) Pulse-length dependence of cellular response to intense near-infrared laser pulses in multiphoton microscopes. *Opt Lett* 24(2): 113-115.
19. Konig K, So P T C, Mantulin W W, & Gratton E (1997) Cellular response to near-infrared femtosecond laser pulses in two-photon microscopes. *Opt Lett* 22(2):135-136.
20. Carling C-J, Nourmohammadian F, Boyer J-C, & Branda N R (2010) Remote-Control Photorelease of Caged Compounds Using Near-Infrared Light and Upconverting Nanoparticles. *Angewandte Chemie, International Edition* 49(22):3782-3785, 53782/3781-53782/3789.
21. Yan B, Boyer J-C, Branda N R, & Zhao Y (2011) Near-Infrared Light-Triggered Dissociation of Block Copolymer Micelles Using Upconverting Nanoparticles. *Journal of the American Chemical Society* 133 (49): 19714-19717.
22. Makadia H K & Siegel S J (2011) Poly lactic-co-glycolic acid (PLGA) as biodegradable controlled drug delivery carrier. *Polymers* (Basel, Switzerland) 3(3):1377-1397.
23. Engineer C, Parikh J, & Raval A (2011) Review on Hydrolytic Degradation Behavior of Biodegradable Polymers from Controlled Drug Delivery System. *Trends Biomater. Artif. Organs* 25(2):79-85.
24. Lei Y, Child J R, & Tsavalas J G (Design and analysis of the homogeneous and heterogeneous distribution of water confined within colloidal polymer particles. *Colloid and Polymer Science*:Ahead of Print.
25. Kumar P, Buldyrev S V, Starr F W, Giovambattista N, & Stanley H E (2005) Thermodynamics, structure, and dynamics of water confined between hydrophobic plates. *Physical Review E: Statistical, Nonlinear, and Soft Matter Physics* 72(5-1):051503/051501-051503/051512.
26. Chaban V V, Prezhdo V V, & Prezhdo O V (2012) Confinement by Carbon Nanotubes Drastically Alters the Boiling and Critical Behavior of Water Droplets. *ACS Nano* 6(3):2766-2773.
27. Giovambattista N, Rossky P J, & Debenedetti P G (2009) Phase Transitions Induced by Nanoconfinement in Liquid Water. *Physical Review Letters* 102(5):050603/050601-050603/050604.
28. Han S, Choi M Y, Kumar P, & Stanley H E (2010) Phase transitions in confined water nanofilms. *Nature Physics* 6(9):685-689.
29. Bisyarin V P, Kolosov M A, Pozhidaev V N, & Sokolov A V (1977) Interaction of ultraviolet, visible, and infrared laser radiation with a water aerosol. (Translated from Russian) *Izvestiya Vysshikh Uchebnykh Zavedenii, Fizika* 20(11):132-153 (in Russian).
30. Chaban V V & Prezhdo O V (2011) Water Boiling Inside Carbon Nanotubes: Toward Efficient Drug Release. *ACS Nano* 5(7):5647-5655.
31. Neumann J & Brinkmann R (2008) Self-limited growth of laser-induced vapor bubbles around single microabsorbers. *Applied Physics Letters* 93(3):033901/033901-033901/033903.
32. Sageev G & Seinfeld J H (1984) Laser heating of an aqueous aerosol particle. *Applied Optics* 23(23):4368-4374.
33. Trigub V A (2010) Estimation of electromagnetic energy accumulation time in a water drop exposed to infrared laser radiation. *Technical Physics* 55(3):409-412.
34. Tsai C-L, Chen J-C, & Wang W-J (1998) Absorption properties of soft tissue constituents in 900-1340 nm region. *Proceedings of SPIE—The International Society for Optical Engineering* 3257(Infrared Spectroscopy: New Tool in Medicine):118-125.
35. Johnston A P R, Such G K, & Caruso F (2010) Triggering Release of Encapsulated Cargo. *Angewandte Chemie, International Edition* 49(15):2664-2666.
36. Blaiszik B J, et al. (2010) Self-Healing Polymers and Composites. *Annu Rev Mater Res* 40:179-211.
37. Dinarvand R, Sepehri N, Manoochehri S, Rouhani H, & Atyabi F (2011) Polylactide-co-glycolide nanoparticles for controlled delivery of anticancer agents. *International Journal of Nanomedicine* 6:877-895.
38. Fredenberg S, Wahlgren M, Reslow M, & Axelsson A (2011) The mechanisms of drug release in poly(lactic-co-glycolic acid)-based drug delivery systems-A review. *Int J Pharmaceut* 415(1-2):34-52.
39. Bock N, Woodruff M A, Hutmacher D W, & Dargaville T R (2011) Electrospraying, a reproducible method for production of polymeric microspheres for biomedical applications. *Polymers* (Basel, Switzerland) 3 (1): 131-149.
40. Siegel S J, et al. (2006) Effect of drug type on the degradation rate of PLGA matrices. *European Journal of Pharmaceutics and Biopharmaceutics* 64(3):287-293.
41. Abraham E, Minoshima K, & Matsumoto H (2000) Femtosecond laser-induced breakdown in water: time-resolved shadow imaging and two-color interferometric imaging. *Opt Commun* 176(4-6):441-452.
42. Glezer E N, Schaffer C B, Nishimura N, & Mazur E (1997) Minimally disruptive laser-induced breakdown in water. *Opt Lett* 22(23): 1817-1819.
43. Imhof A, et al. (1999) Spectroscopy of Fluorescein (FITC) Dyed Colloidal Silica Spheres. *Journal of Physical Chemistry B* 103 (9): 1408-1415.
44. Santra S, Wang K, Tapec R, & Tan W (2001) Development of novel dye-doped silica nanoparticles for biomarker application. *Journal of Biomedical Optics* 6(2): 160-166.
45. Rovers S A, Hoogenboom R, Kemmere M F, & Keurentjes J T F (2012) Repetitive on-demand drug release by magnetic heating of iron oxide containing polymeric implants. *Soft Matter* 8(5):1623-1627.
46. Keurentjes J T F, et al. (2009) Externally Triggered Glass Transition Switch for Localized On-Demand Drug Delivery. *Angewandte Chemie, International Edition* 48(52): 9867-9870, 59867/9861-59867/9868.
47. Tsavalas J G & Sundberg D C (2010) Hydroplasticization of Polymers: Model Predictions and Application to Emulsion Polymers. *Langmuir* 26(10):6960-6966.
48. Chou C-H, Chen C-D, & Wang C R C (2005) Highly Efficient, Wavelength-Tunable, Gold Nanoparticle Based Optothermal Nanoconvertors. *Journal of Physical Chemistry B* 109(22):11135-11138.

What is claimed is:
1. A method for delivering a payload, comprising:
encapsulating the payload in a nanocarrier comprising a hydrophilic polymer having no inherent light sensitivity, wherein the polymer is poly(lactic-co-glycolic) (PLGA);
hydrating the polymer to form nanodomains of water; and
exposing the nanocarrier to light having a wavelength corresponding to a water absorption band within the near infrared (NIR) region adapted to induce resonant photon interactions with the water to locally heat the polymer to induce a phase change in the polymer whereby the payload diffuses out of the nanocarrier.

2. The method of claim 1, wherein the a wavelength is selected from the group consisting of 980 nm, 1200 nm, 1450 nm, and 1950 nm.

3. The method of claim 1, wherein the PLGA has a lactide:glycolide ratio selected according to a desired release rate.

4. The method of claim 3, wherein the lactide:glycolide ratio is selected from the group consisting of 50:50, 75:25, and 85:15.

5. The method of claim 3, wherein the PLGA has a lactide:glycolide ratio selected according to a desired particle size.

6. The method of claim 5, wherein the lactide:glycolide ratio is selected from the group consisting of 50:50, 75:25, and 85:15.

7. The method of claim 1, wherein the payload comprises a therapeutic compound.

8. The method of claim 1, wherein the payload comprises a dye.

9. The method of claim 1, further comprising forming an aggregation of nanocarriers for delivery of the payload over an extended period of time.

* * * * *